US00PP34215P2

(12) United States Plant Patent
Growns

(10) Patent No.: US PP34,215 P2
(45) Date of Patent: May 10, 2022

(54) ***GREVILLEA* PLANT NAMED 'ETERNAL PINK GLORY'**

(50) Latin Name: ***Grevillea* hybrid**
Varietal Denomination: Eternal Pink Glory

(71) Applicant: Botanic Gardens and Parks Authority, Perth (AU)

(72) Inventor: Digby James Growns, Perth (AU)

(73) Assignee: BOTANIC GARDENS AND PARKS AUTHORITY, Perth (AU)

( * ) Notice: Subject to any disclaimer, the term of this patent is extended or adjusted under 35 U.S.C. 154(b) by 0 days.

(21) Appl. No.: 17/136,086

(22) Filed: Dec. 29, 2020

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 6/00
See application file for complete search history.

*Primary Examiner* — Anne Marie Grunberg
(74) *Attorney, Agent, or Firm* — Panitch Schwarze Belisario & Nadel LLP; Stephany G. Small; Travis W. Bliss

(57) ABSTRACT

A new and distinct variety of *Grevillea* Plant, referred to by its cultivar name, 'Eternal Pink Glory', is disclosed. The new variety forms attractive, hot pink colored flowers. Bluish-green colored foliage is formed. The vegetation is moderately vigorous, and the growth habit is upright. The new variety is particularly well suited for providing distinctive ornamentation in the landscape.

1 Drawing Sheet

Botanical/commercial classification:
Latin name: *Grevillea* hybrid.
Varietal denomination: 'Eternal Pink Glory'.

SUMMARY OF THE INVENTION

The new variety of *Grevillea* plant, botanically known as *Grevillea* hybrid, of the present invention originated by cross pollination in Perth, Western Australia, wherein two parents were crossed which previously had been studied in the hope that they would contribute the desired characteristics. The female parent (i.e., the seed parent) was the '20091491' variety (not patented). The male parent (i.e., the pollen parent) was the *Grevillea oligomera* '20060976' variety (not patented).

The parentage can be summarized as follows:

'20091491' x '20060976'

The new cultivar was discovered and selected as a single flowering plant within the progeny of the above stated cross pollination during October 2011 in a controlled environment in Perth, Western Australia.

It was found that the new variety of *Grevillea* plant of the present invention possesses the following combination of characteristics:

(a) forms hot pink colored flowers with pink styles and blue-violet stigmas,
(b) exhibits bluish-green colored foliage with prickly tips,
(c) provides moderately vigorous vegetation, and
(d) forms upright growth habit.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the '20091491' variety (i.e., the seed parent) displays green colored foliage and pink and green colored flowers, whereas the new variety displays bluish-green colored foliage and hot pink colored flowers. The '20060976' variety (i.e., the pollen parent) displays green colored foliage and pink and blue colored flowers, whereas the new variety displays bluish-green colored foliage and hot pink colored flowers. Moreover, the new variety can be readily distinguished from other similar non-parental varieties. For example, the 'Misty Pink' variety (non-patented) exhibits weaker pink flower color and foliage that is less pointed in shape compared to the new variety.

The new variety has been found to undergo asexual propagation in Perth, Western Australia by stem cuttings since October 2011. Asexual propagation by stem cuttings in Perth, Western Australia has shown that the characteristics of the new variety are homogeneous, stable, and strictly transmissible by such asexual propagation from one generation to another. Accordingly, the new variety undergoes asexual propagation in a true-to-type manner.

The new variety has been named 'Eternal Pink Glory'.

BRIEF DESCRIPTION OF THE PHOTOGRAPH

The accompanying photograph shows, as nearly true as it is reasonably possible to make the same in color illustrations of this character, a typical specimen of the new variety. Colors in the photograph differ slightly from the color designations cited in the detailed description, which accurately describes the colors of the new variety. The plant was grown in a container in May 2018 in an outdoor nursery in Valley Center, Calif.

Drawing—illustrates a specimen of the flower—close-up view.

DETAILED BOTANICAL DESCRIPTION

The chart used in the identification of colors described herein is that of The Royal Horticultural Society (R.H.S. Colour Chart) London, England, 2001 edition, except where general color terms of ordinary significance are used. The terminology which precedes reference to the chart has been added to indicate the corresponding color in more common terms. The following measurements and numerical values represent averages of typical plants.

Propagation:

*Type cutting*.—Terminal stem cuttings.

*Time to initiate roots*.—Approximately 14 to 18 weeks.

*Time to produce a rooted cutting*.—Approximately 22 to 26 weeks.

*Root description*.—Light brown in color, fine.

*Rooting habit*.—Freely branching, tight grouping of small roots.

Plant:

*Growth habit and general appearance*.—Moderately vigorous, upright, bushy with blue tinged foliage.

*Size*.—Height: approximately 4.0 m after five years of age. — Width: approximately 3.0 m after five years of age.

*Branching habit*.—Freely upright branching. — Quantity of branches per plant: approximately 14. — Branch Strength: strong. — Lateral branch shape: cross-section is spherical. — Length to base of peduncle: approximately 10.0 cm. — Diameter: approximately 4.0 to 5.0 mm. — Length of central internode: approximately 4.0 cm. — Texture: smooth. — Stem shape: cross-sectional is spherical. — Pubescence color: commonly near White Group 155D. — Color of young stems: commonly near Yellow-Green Group 149D. — Color of mature stems: commonly near Greyed-Orange Group 174A.

Foliage:

*General description*.—Fragrance: none detected.

*Density*.—Spreading.

*Leaf*.—Form: tripinnatisect and terate. — Arrangement: alternate. — Aspect: acute angle to stem. — Attitude: leaf primary lobe in relation to the midrib is erect. — Margin: lobed. — Undulation of leaf margin: absent. — Apex: acute lobes. — Base: attenuate. — Profile of leaf cross section: cylindrical. — Leaf sinus depth of primary division: typically two lobes and the divisions are approximately 3 to 14 cm deep. — Leaf sinus width of primary division: approximately 5 to 8 mm. — Shape of leaf apex of sinus primary division: attenuate. — Leaf lobe of primary division: length is approximately 9 to 10 cm and width is approximately 5 to 14 mm. — Venation pattern: pinnate. — Length of mature leaf: approximately 36.0 cm. — Width of mature leaf: approximately 30.0 cm. — Texture of upper surface: smooth. — Texture of lower surface: smooth. — Pubescence color: commonly near White Group 155A. — Color of upper surface of young foliage: commonly near Green Group 143B. — Color of lower surface of young foliage: commonly near Green Group 143B. — Color of upper surface of mature foliage: commonly near Green Group 138A. — Color of lower surface of mature foliage: commonly near Green Group 138C. — Vein color: upper and lower sides are commonly near Yellow-Green Group 147B.

*Petiole*.—Length: approximately 2 to 6 cm. — Width: approximately 1 to 2 mm. — Texture: glaborous or very sparsely silky. — Color: commonly near Yellow-Green Group 147B.

*Stipule*.—Arrangement: alternate. — Texture: lightly pubescent. — Shape: intrapetiolar. — Length: approximately 1.4 to 2.0 mm. — Color: commonly near Green Group 143C.

Flower:

*Flowering habit*.—Freely flowering habit in full sun outdoor conditions with almost continuous blooming in Zones 8-11.

*Lastingness of individual inflorescence on the plant/flower persistence*.—Approximately 3 to 4 weeks.

Inflorescence description:

*General description*.—Type: raceme. — Shape: cylindrical raceme. — Aspect: facing upward. — Arrangement: terminal and from leaf axils. — Fragrance: none detected. — Quantity per plant: approximately 3. — Flower diameter: approximately 6.0 cm. — Flower depth: approximately 8.0 cm. — Attitude of tepal limb in relation to the longitudinal axis of the flower bud: upright.

*Bud*.—Rate of opening: approximately 2 to 3 days. — Shape: ovoid. — Diameter: approximately 2.0 cm. — Texture of outer surface: pubescent. — Pubescence color: commonly near Greyed-Green Group 194D. — Color: commonly near Green Group 138D.

*Florets*.—Quantity per inflorescence: approximately 80 to 100. — Arrangement: cylindrical. — Length: approximately 15 mm. — Diameter: approximately 1.0 mm.

*Perianth*.—Shape: tubular with a ventral limb that becomes revolute during anthesis. — Length: approximately 2.0 to 3.0 cm. — Diameter at widest point: approximately 1.0 cm. — Diameter as base: approximately 0.5 mm. — Coherence of tepals on the dorsal side: one third to two thirds.

*Tepals*.—Quantity: 4. — Shape: linear. — Margin: entire. — Apex: angle. — Length: approximately 5.0 to 8.0 mm. — Width: approximately 0.5 mm. — Texture of outer surface: pubescent. — Texture of inner surface: smooth. — Color of outer surface when fully open: commonly near Greyed-Green Group 191B. — Color of inner surface when fully open: commonly near Greyed-Green Group 191B.

*Peduncle*.—Strength: strong. — Aspect: erect. — Length: approximately 4.0 to 6.0 cm. — Diameter: approximately 0.75 mm. — Texture: pubescent. — Color: commonly near Yellow-Green Group 144B.

*Rachis*.—Strength: strong. — Length: approximately 10.0 to 12.0 cm. — Diameter: approximately 1.0 to 1.5 mm. — Texture of outer surface: pubescent. — Pubescence color: commonly near Greyed-Green Group 194C.

*Pedicel*.—Strength: strong. — Aspect: upright. — Length: approximately 2.0 mm. — Diameter: approximately 0.4 mm. — Texture of outer surface: pubescent — Pubescence color: commonly near Greyed-Green Group 194D. — Color: commonly near Yellow-Green Group 144C.

*Reproductive organs*.—Anther quantity: 2 per floret. — Anther Shape: bilobed. — Anther length: approximately 2.0 mm. — Anther color: commonly near Greyed-Orange Group 175C. — Pollen amount: scant. — Pollen color: commonly near Greyed-Yellow Group 162A. — Pistil quantity: 1 per floret. — Pistil length: approximately 6.0 to 8.0 cm and is twice the length of the perianth. — Stigma shape: ovoid. — Stigma length: approximately 3.0 to 5.0 mm. — Stigma color: commonly near Violet Group N88B. — Style length: approximately 4.0 to 5.0 cm. — Style color: commonly near Red-Purple Group 73A. — Style curvature: straight. — Style hairiness: sparse and distribution of style hair is concentrated towards the ovary end. — Attitude of pollen presenter to style: lateral. — Ovary length: approximately 0.5 to 0.75 mm. — Ovary texture: pubescent. — Ovary pubescence color: commonly near Green-White Group 157D. — Ovary color: commonly near Yellow-Orange Group 16C. — Nectary length: approximately 0.2 to 0.3 mm. — Nectary width: approximately 0.75 mm. — Nectary color: commonly near White Group 155A.

*Seed*.—Not observed to date.

Development:

*Disease and pest resistance*.—Resistance to pathogens and pests common to *Grevillea* has not been observed.

*Commercial crop time*.—Approximately 18 months.

*Hardiness*.—USDA Zone 8 through 11.

Plants of the 'Eternal Pink Glory' variety have not been observed under all possible environmental conditions to date. Accordingly, it is possible that the phenotypic expression may vary somewhat with changes in light intensity and duration, cultural practices, and other environmental conditions.

I claim:

1. A new and distinct *Grevillea* plant named 'Eternal Pink Glory' characterized by the following combination of characteristics:

(a) forms hot pink colored flowers with pink styles and blue-violet stigmas, (b) exhibits bluish-green colored foliage with prickly tips, (c) provides moderately vigorous vegetation, and (d) forms upright growth habit;

substantially as herein shown and described.

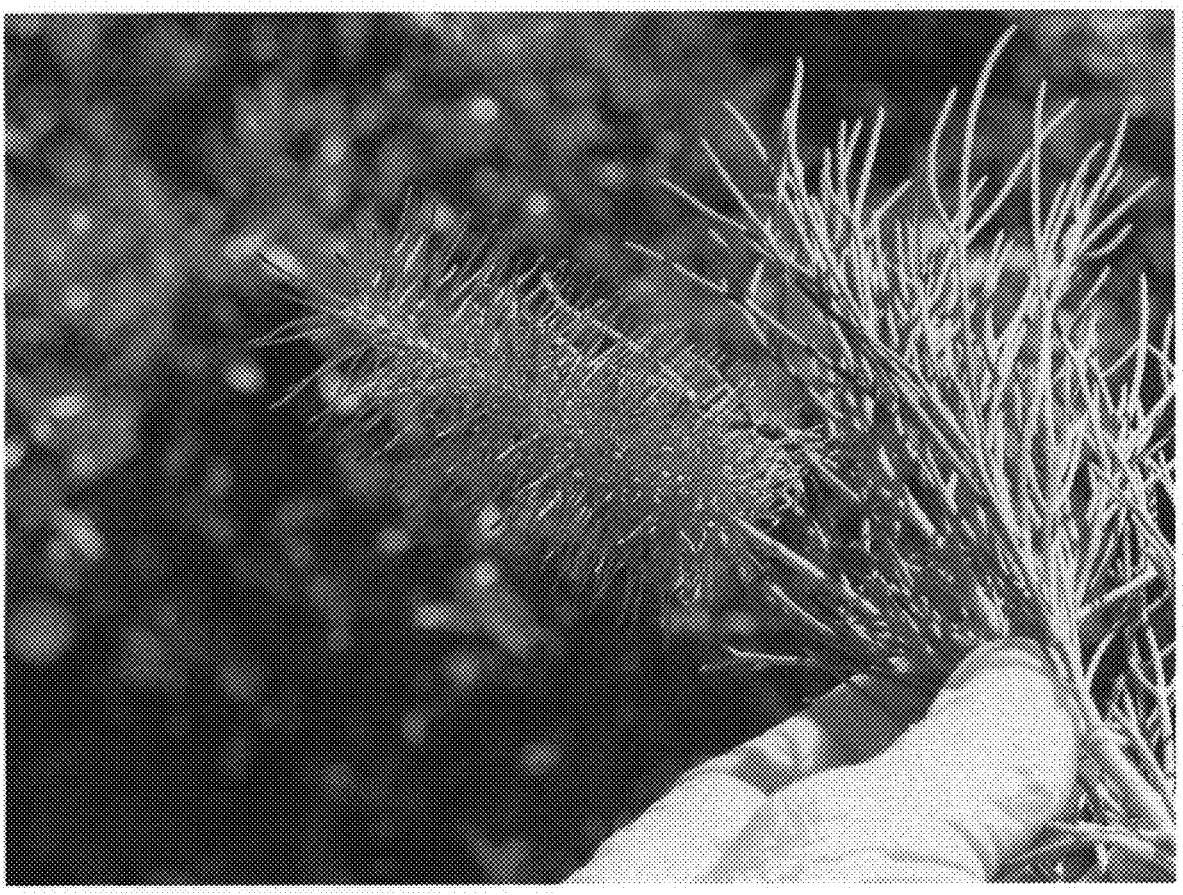

* * * * *